United States Patent [19]

Wright et al.

[11] 4,002,608

[45] Jan. 11, 1977

[54] 1-N-ALKYL-AMINOGLYCOSIDE-XK-88 DERIVATIVES AND METHODS FOR THEIR MANUFACTURE

[75] Inventors: John J. Wright; Peter J. L. Daniels, both of Cedar Grove; Alan K. Mallams, West Orange; Tattanahalli L. Nagabhushan, Parsippany, all of N.J.

[73] Assignee: Schering Corporation, Kenilworth, N.J.

[22] Filed: Nov. 4, 1975

[21] Appl. No.: 628,638

[52] U.S. Cl. .............................. 536/17; 195/80 R; 424/180; 424/181; 536/4
[51] Int. Cl.² ...................................... C07H 15/22
[58] Field of Search ........................... 260/210 AB

[56] References Cited
UNITED STATES PATENTS 3,350,387   10/1967   Vanderhaeghe ............ 260/210 AB

*Primary Examiner*—Johnnie R. Brown
*Attorney, Agent, or Firm*—Mary S. King

[57] ABSTRACT

1-N-Alkyl-Aminoglycoside-XK-88 derivatives, valuable as antibacterial agents, are prepared by the reaction of an acid addition salt of the corresponding 1-N-unsubstituted-Aminoglycoside-XK-88 antibacterial derivative or of a 2''-N-alkanoyl-Aminoglycoside-XK-88-5 derivative in an inert solvent, preferably a protic solvent containing water, with one equivalent of a hydride-donor reducing agent and with at least one equivalent of an aldehyde.

The 2''-N-alkanoyl-Aminoglycoside-XK-88-5 intermediates are prepared by the reaction of a partially neutralized acid addition salt of Aminoglycoside-XK-88-5 with an acylating agent, and isolating the 2''-N-alkanoyl-Aminoglycoside-XK-88-5.

8 Claims, No Drawings

1-N-ALKYL-AMINOGLYCOSIDE-XK-88 DERIVATIVES AND METHODS FOR THEIR MANUFACTURE

FIELD OF INVENTION

This invention relates to novel compositions-of-matter, to methods for their manufacture, and to methods for their use as antibacterial agents.

More specifically, this invention relates to novel 1-N-alkyl-Aminoglycoside-XK-88 derivatives having antibacterial activity, to methods for their manufacture, to pharmaceutical compositions comprising said 1-N-alkyl-Aminoglycoside-XK-88 derivatives and to methods for their use in treating bacterial infections.

In particular, this invention relates to 1-N-alkyl derivatives of Aminoglycoside-XK-88-1, Aminoglycoside-XK-88-3 and Aminoglycoside-XK-88-5, to process for their preparation, to pharmaceutical compositions comprising said 1-N-alkyl-Aminoglycoside-XK-88 derivatives or their pharmaceutically acceptable acid addition salts, and to the method of using said pharmaceutical compositions to elicit an antibacterial response in a warm blodded animal having a susceptible bacterial infection.

PRIOR ART

Known in the art are broad spectrum antibacterial agents which may be classified chemically as 4,6-di-O-(aminoglycosyl)-2-deoxystreptamines. Antibacterial agents included in this group are those known as Aminoglycoside-XK-88-1, Aminoglycoside-XK-88-3 and Aminoglycoside-XK-88-5.

By our invention we have discovered methods whereby the amino group at the 1-position of the 2-deoxystreptamine in said Aminoglycoside-XK-88 antibacterial agents is selectively N-alkylated. We have discovered also that the 1-N-alkyl-4,6-di-O-(aminoglycosyl)-2-deoxystreptamines thereby produced are valuable, broad spectrum antibacterial agents possessing improved therapeutic indexes of antibacterial activities compared to the parent antibiotics. Preferred compounds of our invention include 1-N-lower alkyl-Aminoglycoside-XK-88-5 wherein said alkyl group has up to 4 carbon atoms, particularly the 1-N-ethyl, 1-N-propyl, 1-N-(γ-aminopropyl) and 1-N-(δ-aminobutyl) derivatives.

Known in the art is a process for preparing 1-N-acyl derivatives of 4,6-di-O-(aminoglycosyl)-2-deoxystreptamine antibiotics which comprises the reaction of a partially neutralized acid addition salt of said 4,6di-O-(aminoglycosyl)-2-deoxystreptamine with an acylating agent which may optionally bear a hydroxy and/or an amino substituent, and isolating the 1-N-acyl derivative thereby formed.

By our invention, we have found that when a partially neutralized salt of Aminoglycoside-XK-88-5 is reacted with an acylating agent, there is formed predominately a 2''-N-acyl-Aminoglycoside-XK-88-5 derivative, useful as an intermediate in the preparation of 1-N-alkyl-Aminoglycoside-XK-88-5.

GENERAL DESCRIPTION OF THE INVENTION
COMPOSITION-OF-MATTER ASPECT

Included among the antibacterially active compositions-of-matter of this invention are 1-N-X-4,6-di-O-(aminoglycosyl)-2-deoxystreptamines selected from the group consisting of 1-N-X-Aminoglycoside-XK-88-1, 1-N-X-Aminoglycoside-XK-88-3 and 1-N-X-Aminoglycoside-XK-88-5;

wherein X is an alkyl substituent selected from the group consisting of alkyl, alkenyl, aralkyl, cycloalkylalkyl, hydroxyalkyl, aminoalkyl, alkylaminoalkyl, aminohydroxyalkyl, and alkylaminohydroxyalkyl, said alkyl substituent preferably having up to 8 carbon atoms, the carbon atom in said alkyl substituent adjacent to the aminoglycoside nitrogen atom being unsubstituted, and when said alkyl substituent is substituted by both hydroxyl and amino functions, only one of said hydroxyl and amino functions can be attached to any one carbon atom;

and the pharmaceutically acceptable acid addition salts thereof.

Included among the alkyl substituents contemplated for the moiety X in our novel compounds are straight and branched chain alkyl groups such as ethyl, n-propyl, n-butyl, β-methylpropyl, n-pentyl, β-methylbutyl, γ-methylbutyl and β,β-dimethylpropyl; n-hexyl, δ-methylpentyl, β-ethylbutyl, γ-ethylbutyl, n-heptyl, ε-methylheptyl, β-ethylpentyl, γ-ethylpentyl, δ-ethylpentyl, γ-propylbutyl, n-octyl, iso-octyl, β-ethylhexyl, δ-ethylhexyl, ε-ethylhexyl, β-propylpentyl, γ-propylpentyl; cycloalkyl groups such as cyclopropylmethyl, cyclopentylmethyl, cyclohexylmethyl and cyclopentylethyl; alkenyl groups such as β-propenyl, β-methylpropenyl, β-butenyl, β-methyl-β-butenyl, β-ethyl-β-hexenyl; aralkyl groups such as benzyl, o-tolyl, m-tolyl, p-tolyl and phenylethyl; hydroxy substituted straight and branched chain alkyl groups such as ε-hydroxypentyl, β-hydroxy-γ-methylbutyl, β-hydroxy-β-methylpropyl, δ-hydroxybutyl, β-hydroxypropyl, γ-hydroxypropyl, ω-hydroxyoctyl; amino substituted straight and branched chain alkyl groups such as ε-aminopentyl, β-aminopropyl, γ-aminopropyl, δ-aminobutyl, β-amino-ε-methylbutyl and ω-aminooctyl and mono-N-alkylated derivatives thereof such as the N-methyl, N-ethyl, and N-propyl derivatives, e.g. ε-methylaminopentyl, β-methylaminopropyl, β-ethylaminopropyl, δ-methylaminobutyl, β-methylamino-γ-methylbutyl, and ω-methylaminobutyl: amino and hydroxy disubstituted straight and branched chain alkyl groups such as β-hydroxy-ε-aminopentyl, γ-hydroxy-γ-methyl-δ-aminobutyl, β-hydroxy-δδ-aminobutyl, β-hydroxy-ε-aminopropyl, and β-hydroxy-β-methyl-ε-aminopropyl: and mono-N-alkylated derivatives thereof such as β-hydroxy-ε-methylaminopentyl, γ-hydroxy-γ-methyl-δ-methylaminobutyl, β-hydroxy-δ-methylaminobutyl, β-hydroxy-γ-ethylaminopropyl, and β-hydroxy-β-methyl-γ-methyl aminopropyl.

Of the foregoing alkyl substituents contemplated for the moiety X, preferred are lower alkyl substituents having up to 4 carbon atoms, especially those having 2 to 4 carbon atoms, particularly valuable derivatives being 1-N-ethyl, 1-N-propyl, 1-N-(γ-aminopropyl) and 1-N-(δ-aminobutyl)-Aminoglycoside-XK-88 derivatives.

Useful antibacterial agents of our invention are 1-N-X-4,6-di-O-(aminoglycosyl)-2-deoxystreptamines defined by the following structural formulae:

1-N-X-Aminoglycoside-XK-88-1 of formula I:

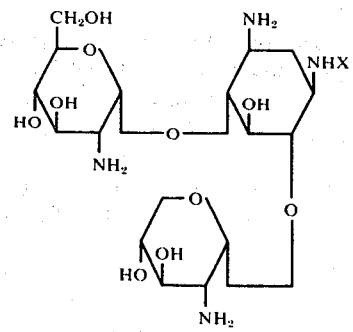

1-N-X-Aminoglycoside-XK-88-3 of formula II:

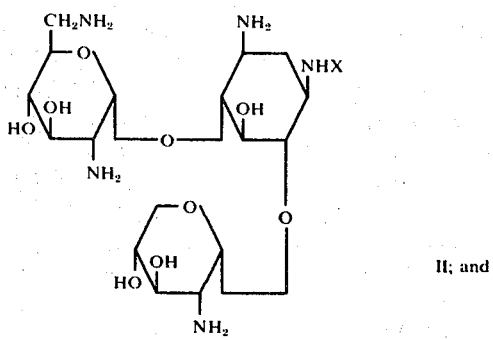

1-N-X-Aminoglycoside-XK-88-5 of formula III:

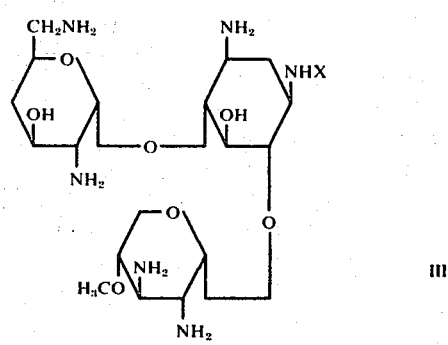

wherein X is as hereinabove defined.

Of the foregoing, preferred are the 1-N-X-aminoglycoside-XK-88-5 derivatives of formula III.

The 1-N-alkyl-4,6-di-0-(aminoglycosyl)-2-deoxystreptamines of this invention as defined by formulae I, II, and III are characterized by being white amorphous powders.

Also included within the composition-of-matter aspect of this invention are pharmaceutically acceptable acid addition salts of the 1-N-X-4,6-di-O-(aminoglycosyl)-2-deoxystreptamines such as defined by formulae I, II, and III, which salts are made according to known procedures such as by neutralizing the free base with the appropriate acid usually to about pH 5. Suitable acids for this purpose include acids such as hydrobromic, acetic, propionic, and preferably, strong inorganic acids such as hydrochloric, sulfuric and phosphoric acid. The physical embodiments of the acid addition salts of the 1-N-X-4,6-di-O-(aminoglycosyl)-2-deoxystreptamines of this invention are characterized by being white solids which are soluble in water, sparingly soluble in most polar organic solvents and insoluble in most nonpolar organic solvents.

The 1-N-X-4,6-di-O-(aminoglycosyl)-2-deoxystreptamines of this invention such as defined by formulae I, II, and III, (i.e. 1-N-X-Aminoglycoside-XK-88-1, 1-N-X-Aminoglycoside-XK-88-3, and 1-N-X-Aminoglycoside-XK-88-5), and their non-toxic, pharmaceutically acceptable acid addition salts, in general, exhibit broad spectrum antibacterial activity and possess an improved therapeutic index compared to the parent antibiotics.

Particularly useful compounds of our invention are those wherein X is a lower alkyl having up to 8 carbon atoms, particularly those having up to 4 carbon atoms, e.g. compounds of formulae I, II, and III wherein X is methyl, ethyl, n-propyl, n-butyl, β-hydroxyethyl, γ-aminopropyl, δ-aminobutyl, and (S-δ-amino-β-hydroxybutyl). Of these, a particularly valuable group are the 1-N-X-Aminoglycoside-XK-88-5 of formula III wherein X is a lower alkyl having 2 to 4 carbon atoms, particularly the 1-N-ethyl derivatives thereof, which derivatives are broad spectrum antibacterial agents, being active against gram positive bacteria (e.g. Staphylococcus aureus) and gram negative bacteria (e.g. Escherichia coli and Pseudomonas aeruginosa).

GENERAL DESCRIPTION OF THE PROCESS ASPECT OF THE INVENTION

In the process of this invention, the 1-N-X-4,6-di-O(aminoglycosyl)-2-deoxystreptamine defined by formulae I, II, and III, are prepared by treating an acid addition salt of the corresponding 1-N-unsubstituted-4,6-di-O-(aminoglycosyl)-2-deoxystreptamine antibacterial agent, or, preferably, the acid addition salt of 1-N-unsubstituted-2″-N-acetyl-Aminoglycoside-XK-88-5, with about one molar equivalent of a hydride-donor reducing agent in an inert solvent (preferably a protic solvent in the presence of water) and in the presence of at least one molar equivalent of an aldehyde having the formula X′CHO wherein X′ is an alkyl substituent selected from the group consisting of hydrogen, alkyl, alkenyl, aralkyl, hydroxyalkyl, aminoalkyl, alkylaminoalkyl, aminohydroxyalkyl, and alkylaminohydroxyalkyl, said alkyl substituent having up to 7 carbon atoms, and, when said alkyl substituent is substituted by both hydroxyl and amino functions, only one of said functions can be attached to any one carbon atom.

This process, whereby the 1-amino function in an acid addition salt of a 1-N-unsubstituted-4,6-di-O-(aminoglycosyl)-2-deoxystreptamine antibacterial agent is selectively condensed with an aldehyde and concomitantly reduced in situ to form a 1-N-alkyl-4,6-di-O-(aminoglycosyl)-2-deoxystreptamine antibacterial agent, is usually carried out at room temperature in the presence of air, although it may be advantageously carried out under an inert atmosphere (e.g. argon or nitrogen). Advantageously, the reaction is completed within a short time, usually less than 30 minutes, as determined by thin layer chromatography.

Hydride-donor reducing agents useful in our process include dialkylaminoboranes (e.g. dimethylaminoborane, diethylaminoborane and preferably morpholinoborane), tetraalkylammonium cyanoborohydride (e.g. tetrabutylammonium cyanoborohydride), alkali metal borohydride (e.g. sodium borohydride) and preferably, alkali metal cyanoborohydride (e.g.

lithium cyanoborohydride and sodium cyanoborohydride).

Our process is conveniently carried out at ambient temperatures in an inert solvent. By "inert solvent" is meant any organic or inorganic solvent in which the 4,6-di-O-(aminoglycosyl)-2-deoxystreptamine starting compounds and the reagents are soluble, and which will not interfere with the process under the reaction conditions thereof so there are produced a minimum of competing side reactions. Although anhydrous aprotic solvents may sometimes advantageously be employed in our process (such as tetrahydrofuran when utilizing morpholinoborane as hydride-donor reducing agent) we usually carry out our process in protic solvents, e.g. in a lower alkanol or, preferably, in water or in an aqueous lower alkanol (e.g. aqueous methanol, aqueous ethanol), although other water-miscible co-solvent systems may be employed such as aqueous dimethylformamide, aqueous hexamethylphosphoramide, aqueous tetrahydrofuran and aqueous ethylene glycol dimethyl ether.

The acid solution salts of the 1-N-unsubstituted-4,6-di-O-aminoglycosyl)-2-deoxystreptamines, requisite starting compounds of our process, may be derived from any organic acid such as acetic acid, trifluoroacetic acid, or p-toluenesulfonic acid or from any inorganic acid such as hydrochloric acid, sulfuric acid or phosphoric acid. We have found it most convenient to use the addition salts derived from sulfuric acid. In our process, optimum results are achieved when all amino groups present in the molecule are fully neutralized; however, our process may be carried out using 4,6-di-O-(aminoglycosyl)-2-deoxystreptamine acid addition salts which are not fully protonated or, alternatively, on fully protonated compounds in the presence of excess acid. In carrying out our process, we find it convenient to prepare the requisite acid addition salt starting compound in situ by adding the desired acid (e.g. sulfuric acid) to a solution or suspension of the 4,6-di-O-(aminoglycosyl)-2-deoxystreptamine or derivative thereof (e.g. 2''-N-acetyl-Aminoglycoside-XK-88-5) in a protic solvent (e.g. water) until the pH of the solution is in the range of from about 2 to about 5, preferably from about pH 2.5 to about pH 3.5. Our process proceeds best within this range, but may be carried out at pH values in the range of from about pH 1 to about pH 8.

The 4,6-di-O-aminoglycosyl)-2-deoxystreptamine antibacterial precursors for the acid addition salt starting compounds of our invention include Aminoglycoside-XK-88-1, Aminoglycoside-XK-88-3 and Aminoglycoside-XK-88-5, which are known compounds sometimes also identified as Seldomycin Factors 1, 3 and 5, respectively. Their preparation from *Streptomyces hofuensis* ATCC 21970, their isolation, properties, and structures are described in Belgium Pat. No. 821,441 and German Offenlegungsschrift 2450411. When preparing a 1-N-alkyl derivative of Aminoglycoside-XK-88-5, greater yields of desired product are obtained if the amino function at the 2''-position is N-protected (e.g. by an N-alkanoyl group such as N-acetyl) prior to conversion to the acid addition salt thereof and thence reaction with an aldehyde and a hydride-donor reducing agent.

Typical aldehydes of the formula X'CHO wherein X' is as above defined which are useful in our process include straight and branched chain alkyl aldehydes such as formaldehyde, acetaldehyde, n-propanal, n-butanal, 2-methylpropanal, n-pentanal, 2-methylbutanal, 3methylbutanal, 2,2-dimethylpropanal, n-hexenal, 2-ethylbutanal, n-heptanal and n-octanal; alkenyl aldehydes such as propenal, 2-methylpropenal, 2-butenal, 2-methyl-2-butenal, 2-ethyl-2-hexenal; cycloalkyl aldehydes such as cyclopropanecarbaldehyde, cyclopentanecarbaldehyde, cyclopentaneacetaldehyde and cyclohexanecarbaldehyde; aralkyl aldehydes such as benzaldehyde, o, m, and p-tolualdehydes and phenylacetaldehyde; hydroxy substituted straight and branched chain alkyl aldehydes such as 5-hydroxypentanal, 2-hydroxy-3-methylbutanal, 2-hydroxy-2-methylpropanal, 4-hydroxybutanal, 2-hydroxypropanal and 8-hydroxyoctanal: amino substituted straight and branched chain alkyl aldehydes wherein the amino group must be protected prior to reaction in the process described herein, such as 5-aminopentanal, 2-aminopropanal, 3-aminopropanal, 4-aminobutanal, 2-amino-3-methylbutanal, 8-aminooctanal and mono-N-alkyl derivatives thereof; and amino and hydroxy disubstituted straight and branched chain alkyl aldehydes such as 2-hydroxy-5-aminopentanal, 3-hydroxy-3-methyl-4-aminobutanal, 2-hydroxy-4-aminobutanal, 2-hydroxy-3-aminopropanal, 2-hydroxy-2-methyl-3-aminopropanal, 2-amino-3-hydroxyoctanal, and mono-N-alkyl derivatives thereof.

In this process, if the aldehyde possesses a chiral center, one can use each enantiomer separately or together as a racemate and there will be obtained the respective diastereoisomers or a mixture thereof, respectively.

The aldehyde reagents useful in our process are either known compounds or are easily prepared from known compounds utilizing procedures well known in the art. Thus, for example, alkylaldehydes substituted by both hydroxyl and amino functions (e.g. 2-hydroxy-5-aminopentanal) may be prepared from an aminoaldehyde acetal (e.g. 4-aminobutanal diethylacetal) by protecting the amino function therein as an acetamido or phthalimido group utilizing known procedures followed by removal of the acetal function by acid hydrolysis thereby obtaining an N-protected aminoaldehyde (e.g. by converting 4-aminobutanal diethylacetal to the corresponding N-phthalimido derivative which upon acid hydrolysis yields 4-phthalimidobutanal). Treatment of the N-protected aminoaldehyde with hydrocyanic acid yields the corresponding N-protected-aminoalkyl hydroxynitrile (e.g. 2-hydroxy-5-phthalimidovaleronitrile) which upon catalytic reduction (e.g. hydrogen in the presence of palladium) or by hydride reduction (e.g. with diisobutylaluminum hydride) yields an N-protected amino-hydroxy aldehyde (e.g. 2-hydroxy-5-phthalimido-pentanal) which is an aldehyde reagent used in our process.

When carrying out our process whereby an acid addition salt of a 1-N-unsubstituted-4,6-di-O-(aminoglycosyl)-2-deoxystreptamine is treated with a hydride donor and an aldehyde to obtain the corresponding 1-N-alkyl-4,6-di-O-(aminoglycosyl)-2-deoxystreptamine, in order to mininize competing side reactions when an aminoaldehyde is used as reagent, it is necessary to protect the amino function in the aldehyde, e.g. with an acyl blocking group such as acetamido, phthalimido, or the like, prior to carrying out our process, and thence removing the N-protecting group in the 1-N-(protected aminoalkyl)-4,6-di-O-(aminoglycosyl-2-deoxystreptamine thereby produced. It may also be advantageous to protect the hydroxyl group in hydroxyl-containing aldehydes when carrying out our process; however, it is not generally necessary.

A convenient method of carrying out our process comprises preparing a solution of a 1-N-unsubstituted-4,6-di-O-(aminoglycosyl)-2-deoxystreptamine antibacterial agent (e.g. 2''-N-acetyl-Aminoglycoside-XK-88-5) in a protic solvent, (preferably water), and adjusting the pH of the solution to from about pH 2 to about pH 5 with an acid (usually dilute sulfuric acid) thereby preparing the requisite acid addition salt of the starting compound. When the pH of the solution is at about pH 5, the acid addition salt thereby produced usually contains about one equivalent of acid for each amino function in the 4,6-di-O-(amionoglycosyl)-2-deoxystreptamine (e.g. per mole of 2''-N-acetyl-Aminoglycoside-XK-88-5 there is present 2.5 moles of sulfuric acid). After the acid addition salt solution is prepared, there is added at least a molar equivalent, and preferably a large molar excess of the desired alkyl aldehyde (e.g. acetaldehyde) followed within a short time (usually in about 5 minutes) by the addition of about a molar equivalent (based upon the starting 4,6-di-O-(aminoglycosyl)-2-deoxystreptamine) of a hydride-donor reducing reagent, preferably an alkali metal cyanoborohydride, usually sodium cyanoborohydride. The reaction is frequently completed in less than 30 minutes as determined by thin layer chromatography and there is obtained the corresponding 1-N-alkyl-4,6-di-O-(aminoglycosyl)-2-deoxystreptamine acid addition salt (e.g. the acid addition salt of 1-N-ethyl-2''-N-acetyl-Aminoglycoside-XK-88-5) which, upon treatment with base yields the corresponding 1-N-alkyl-4,6-di-O-(aminoglycosyl)-2-deoxystreptamine (e.g. 1-N-ethyl-Aminoglycoside-XK-88-5) having enhanced antibacterial activity.

In the above process, suitable as N-protecting groups at C-2'' of Aminoglycoside-XK-88-5 are those groups known in the art to be easily removable after preparation of 1-N-alkyl-Aminoglycoside-XK-88-5 without affecting the 1-N-alkyl substituents therein. Exemplary of such amino protecting groups are acyl groups such as acetyl, propionyl and benzoyl; alkoxycarbonyl groups such as methoxycarbonyl, ethoxycarbonyl, 2,2,2-trichloroethoxycarbonyl, t-butoxycarbonyl and 2-iodoethoxycarbonyl; and arylalkoxycarbonyl groups such as carbobenzyloxy and 4-methoxybenzyloxycarbonyl groups. Preferred are the lower alkanoyl groups, particularly the 2''-N-acetyl groups.

The 2''-N-lower alkanoyl-Aminoglycoside-XK-88-5 preferred starting compounds for our process for preparing 1-N-lower alkyl-Aminoglycoside-XK-88-5, are prepared by the reaction of a partially neutralized acid addition salt of an Aminoglycoside-XK-88-5 with an acylating agent derived from an alkanoic acid having up to 8 carbon atoms including acylating reagents derived from formic, acetic, propionic, butyric, caproic and caprylic acids.

Preferred acylating agents of this process are the lower alkanoic acid anhydrides, particularly acetic anhydride.

The term "partially neutralized acid addition salt" means that each mole of Aminoglycoside-XK-88-5 has less than a stoichiometric number of moles of acid associated therewith, i.e. has less than the six equivalents of acid which would be required form the "per" acid addition salt.

The acid addition salts useful in this process may be derived from organic acids such as acetic, propionic, succinic, oxalic, cyclopropylcarboxylic, trimethylacetic, maleic, benzoic, phenylacetic, trifluoroacetic or the like; however, preferred acid addition salts are those derived from strong inorganic acids such as phosphoric, hydrochloric and, preferably, sulfuric acid.

A convenient method of carrying out this process comprises preparing a solution of Aminoglycoside-XK-88-5 in an aqueous alkanol (e.g. aqueous methanol), then adding an acid (e.g. sulfuric acid) until the solution is at about pH 6, at which pH the Aminoglycoside-XK-88-5 acid addition salt produced thereby usually contains about five equivalents of acid, although there are six amino groups present. To this partially neutralized acid addition salt is added the acylating agent (e.g. acetic anhydride), the molar quantity of which may be in great excess to the molar quantity of Aminoglycoside-XK-88-5. The reaction mixture is allowed to stand at room temperature until the reaction is complete as determined by thin layer chromatography, then the main product, i.e. the 2''-N-alkanoyl (e.g. the 2''-N-acetyl) derivative of Aminoglycoside-XK-88-5, is isolated utilizing chromatographic techniques.

It is surprising that by this process there is produced mainly 2''-N-alkanoyl-Aminoglycoside-XK-88-5 since, when other 4,6-di-O-(aminoglycosyl)-2-deoxystreptamines, (e.g. gentamicin $C_2$) are reacted in a manner similar to that described hereinabove (e.g. as described in Belgium Pat. No. 824,567), the 1-N-acyl derivative (i.e. 1-N-acetylgentamicin $C_2$) is formed. In Aminoglycoside-XK-88-5 which possesses amino groups at position 2'' as well as at 1, 3, 2', 6' and 3''', however, the 2''-N-alkanoyl derivative is formed in preference to the 1-N-acyl derivative.

The 2''-N-alkanoyl-Aminoglycoside-XK-88-5 derivatives are the preferred starting compounds for preparing the corresponding 1-N-alkyl-Aminoglycoside-XK-88-5 derivative by reaction with an aldehyde and thence a borohydride reducing agent at pH 1 to 8 as described hereinabove. The resulting 1-N-alkyl-2''-N-alkanoyl-Aminoglycoside-XK-88-5 is then reacted with base at elevated temperatures for long periods of time to remove the 2''-N-alkanoyl protecting group.

The process described hereinabove is illustrated in detail hereinbelow which should not be construed as limiting the scope of our invention.

PREPARATION 1

2''-N-ALKANOYL-AMINOGLYCOSIDE-XK-88-5

A. 2''-N-Acetyl-Aminoglycoside-XK-88-5

To a solution of aminoglycoside-XK-88-5 (1.25 gms.) in 200 ml. of methanol:water (2:3, v/v) add 1 N sulfuric acid until the solution is at about pH 6. Add acetic anhydride (1.25 ml.) and allow the solution to stand at room temperature for 2 hours. Concentrate the solution in vacuo, dissolve the resultant residue in water and pass the aqueous solution through basic ion exchange resin (e.g. Amberlite IRA-401S (OH$^-$), then lyophilize the eluate and chromatograph the resultant residue on 50 gms. of silica gel eluting with the lower phase of a chloroform: methanol:10% ammonium hydroxide solvent system (2:1:1). Combine the like eluates containing 2''-N-acetyl-Aminoglycoside-XK-88-5 as determined by thin layer chromatography and concentrate the combined eluates in vacuo to a residue comprising 2''-N-acetyl-Aminoglycoside-XK-88-5.

B. In the procedure of Preparation 1A by substituting for acetic anhydride the anhydride of other lower alkanoic acids, e.g. propionic acid anhydride and N-butyric anhydride, there is obtained the corresponding 2''-N-alkanoyl derivative, e.g. 2''-N-propionyl-Aminoglycoside-XK-88-5 and 2''-N-butyryl-Aminoglycoside-XK-88-5, respectively.

PREPARATION 2

PREPARATION OF ALDEHYDE INTERMEDIATES

A. 2-Acetamido-3-Hydroxyoctanal

Protect the amino function in the 2-amino-3-hydroxyoctanoic acid by conversion thereof to an acetamido function, then esterify the resultant 2-acetamido-3-hydroxyoctanoic acid with methanol; reduce the resultant 2-acetamido-3-hydroxyoctanoic acid methyl ester with di-isobutylaluminum hydride according to known procedures to obtain 2-acetamido-3-hydroxyoctanal.

B. 2-Acetoxy-4-(N-Methylacetamido)Butanal

Treat the diethylacetal of 2-hydroxy-4-aminobutanal with acetic anhydride in pyridine followed by treatment of the resulting diethylacetal of 2-acetoxy-4-acetamidobutanal with sodium hydride and methyl iodide to obtain the diethylacetal of 2-acetoxy-4-(N-methylacetamido)butanal. Remove the acetal protecting group by means of acid to obtain 2-acetoxy-4-(N-methylacetamido)butanal.

EXAMPLE 1

1-N-ALKYL-AMINOGLYCOSIDE-XK-88-5

A. 1-N-Ethyl-Aminoglycoside-XK-88-5

1. To a solution of 0.5 gms. of 2''-N-acetyl-Aminoglycoside-XK-88-5 in 25 ml. of water add 1 N sulfuric acid until the pH of the solution is adjusted to about between 2.5 and 3.5. To the solution of 2''-N-acetyl-Aminoglycoside-XK-88-5 sulfuric acid addition salt thereby formed, add 0.2 ml. of acetaldehyde, stir for 10 minutes, then add 75 mgm. of sodium cyanoborohydride. Continue stirring at room temperature for 30 minutes, then concentrate the solution in vacuo to a volume of about 10 ml., treat the solution with a basic ion exchange resin (e.g. Amberlite IRA-401S (OH⁻)), then lyophilize to a residue comprising 1-N-ethyl-2''-N-acetyl-Aminoglycoside-XK-88-5.

Purify by chromatographing on 25 gm. of silica gel, eluting with the lower phase of a chloroform:methanol:10% aqueous ammonium hydroxide (2:1:1) system. Combine the like eluates as determined by thin layer chromatography and concentrate the combined eluates of the major component in vacuo to a residue comprising 1-N-ethyl-2''-N-acetyl-Aminoglycoside-XK-88-5.

2. Dissolve 1-N-ethyl-2''-N-acetyl-Aminoglycoside-XK-88-5 (0.25 gms.) in 1 N sodium hydroxide (5 ml.), and heat at reflux temperature under an atmosphere of nitrogen for 100 hours. Cool the solution and add 1 N hydrochloric acid until the pH is between 10 and 11. Concentrate the solution to a volume of about 1 ml., pour the residue into anhydrous ethanol, filter, evaporate the filtrate, and chromatograph the resultant residue on silica gel eluting with the lower phase of a chloroform:methanol:10% ammonium hydroxide solvent system (2:1:1). Monitor the fractions by thin layer chromatography, combine the like fractions containing 1-N-ethyl-Aminoglycoside-XK-88-5, evaporate the combined fractions to a residue comprising 1-N-ethyl-Aminoglycoside-XK-88-5.

B. In the procedure of above Example 1A instead of adding 1 N sulfuric acid to the solution of 2''-N-acetyl-Aminoglycoside-XK-88-5 in water until it reaches a pH of about 2.5 to 3.5, other acids may be used, such as acetic acid, trifluoroacetic acid, p-toluenesulfonic acid, hydrochloric acid or phosphoric acid. The acidified aqueous solution is then treated with acetaldehyde and sodium cyanoborohydride and the resultant product is treated with basic ion exchange resin, then treated with sodium hydroxide and purified as described in Example 1B whereby is obtained 1-N-ethyl-Aminoglycoside-XK-88-5.

C. Alternatively, in the procedure of Example 1A, replace sodium cyanoborohydride with an equivalent quantity of other hydridedonor reducing agents, (for example, with morpholinoborane, tetrabutylammonium cyanoborohydride, or sodium borohydride), to obtain 1-N-ethyl-Aminoglycoside-XK-88-5.

D. 1-N-Methyl-Aminoglycoside-XK-88-5

1. To a solution of 4.64 gms. of 2''-N-acetyl-Aminoglycoside-XK-88-5 in 180 ml. of water add 1 N sulfuric acid until the solution is at a pH of about 2.5 to 3.5. Add 1.2 ml. of 37% aqueous formaldehyde, stir at room temperature for 30 minutes, then add 460 mg. of sodium cyanoborohydride. Pass the reaction solution through a column of a basic ion exchange resin (e.g. Amberlite IRA-401S (OH⁻ form)) and lyophilize. Chromatograph the resultant residue on silica gel in the lower phase of a chloroform:methanol: 7% aqueous ammonium hydroxide (2:1:1) solvent mixture. Combine the like eluates containing substantially 1-N-methyl-2''-N-acetyl-Aminoglycoside-XK-88-5 as determined by thin layer chromatography. Evaporate in vacuo to a residue of 1-N-methyl-2''-N-acetyl-Aminoglycoside-XK-88-5.

2. Treat the foregoing product with aqueous sodium hydroxide in the manner of Example 1A(2) to obtain 1-N-methyl-Aminoglycoside-XK-88-5.

E. Other 1-N-Alkyl, 1-N-Alkenyl and 1-N-Aralkyl-Aminoglycoside-XK-88-5 Derivatives In the procedure of Example 1A, instead of acetaldehyde, substitute equivalent amounts of each of the following alkyl aldehydes:
1. propanal,
2. n-butanal,
3. 2-methylpropanal,
4. n-pentanal,
5. 3-methylbutanal,
6. 2-methylbutanal,
7. 2,2-dimethylpropanal,
8. 2-ethylbutanal,
9. n-octanal,
10. propenal,
11. 2-ethyl-2-hexenal,
12. benzaldehyde, and
13. phenylacetaldehyde.

In each case carry out the reaction in a manner similar to that described in Example 1A, isolate and purify each of the resultant products in a manner similar to that described in Example 1A, then treat each of the resultant 1-N-alkyl-2''-N-acetyl derivatives with sodium hydroxide in the manner of Example 1A(2) to obtain, respectively,
1. 1-N-propyl-Aminoglycoside-XK-88-5,
2. 1-N-(n-butyl)-Aminoglycoside-XK-88-5,
3. 1-N-(β-methylpropyl)-Aminoglycoside-XK-88-5,
4. 1-N-(n-pentyl)-Aminoglycoside-XK-88-5,
5. 1-N-(γ-methylbutyl)-Aminoglycoside-XK-88-5, 6. 1-N-(β-methylbutyl)-Aminoglycoside-XK-88-5,
7. 1-N-(β,β-dimethylpropyl)-Aminoglycoside-XK-88-5,
8. 1-N-(β-ethylbutyl)-Aminoglycoside-XK-88-5,
9. 1-N-(n-octyl)-Aminoglycoside-XK-88-5,
10. 1-N-(β-propenyl)-Aminoglycoside-XK-88-5,
11. 1-N-(β-ethyl-β-hexenyl)-Aminoglycoside-XK-88-5,
12. 1-N-benzyl-Aminoglycoside-XK-88-5, and
13. 1-N-phenylethyl-Aminoglycoside-XK-88-5.

F. 1-N-(Hydroxyalkyl)-Aminoglycoside-XK-88-5 Derivatives

In the procedure of Example 1A, instead of acetaldehyde, substitute equivalent amounts of each of the following aldehydes:
1. 5-hydroxypentanal,
2. 2-hydroxypropanal,
3. 2-hydroxy-3-methylbutanal,
4. 2-hydroxy-2-methylpropanal,
5. 4-hydroxybutanal,
6. 8-hydroxyoctanal, and
7. 2-hydroxy-4-pentenal.

In each case carry out the reaction in a manner similar to that described in Example 1A, and isolate and purify each of the resultant products in a manner similar to that described in Example 1A followed by reaction of the resulting 1-N-(hydroxyalkyl)-2''-N-acetyl-Aminoglycoside-XK-88-5 with aqueous sodium hydroxide in the manner of Example 1A(2) to obtain, respectively,
1. 1-N-(ε-hydroxypentyl)-Aminoglycoside-XK-88-5,
2. 1-N-(β-hydroxypropyl)-Aminoglycoside-XK-88-5,
3. 1-N-(β-hydroxy-γ-methylbutyl)-Aminoglycoside-XK-88-5,
4. 1-N-(β-hydroxy-β-methylpropyl)-Aminoglycoside-XK-88-5,
5. 1-N-(δ-hydroxybutyl)-Aminoglycoside-XK-88-5,
6. 1-N-(ω-hydroxyoctyl)-Aminoglycoside-XK-88-5, and
7. 1-N-(β-hydroxy-δ-pentenyl)-Aminoglycoside-XK-88-5.

G. 1-N-(δ-Aminobutyl)-Aminoglycoside-XK-88-5.

1. Add 1 N sulfuric acid dropwise to a solution of 3 gms. of 2''-N-aacetyl-Aminoglycoside-XK-88-5 in 120 ml. of water until the pH of the solution is adjusted to about 2.5 – 3.5. To the aqueous solution of the sulfuric acid addition salt of 2''-N-acetyl-Aminoglycoside-XK-88-5 thereby formed, add 60 ml. of dimethylformamide followed by a solution of 2 gms. of 4-phthalimidobutanal in 10 ml. of dimethylformamide. Continue stirring for 10 minutes, then add 420 mg. of sodium cyanoborohydride. After about 20 minutes, add the reaction solution to 1 liter of anhydrous methanol with stirring and collect by filtration the resultant precipitate comprising the sulfuric acid addition salt of 1-N-(δ-phthalimidobutyl)-2''-N-acetyl-Aminoglycoside-XK-88-5.

2. Purify by dissolving the precipitate in water and passing the aqueous solution over a basic ion exchange resin. Evaporate in vacuo to a residue, chromatograph the residue over silica gel eluting with the lower phase of a chloroform:methanol:7% aqueous ammonium hydroxide (2:1:1) solvent mixture, and evaporate the combined, like eluates to a residue comprising 1-N-(δ-phthalimidobutyl)-2''-N-acetyl-Aminoglycoside-XK-88-5.

To 0.5 gms. of 1-N-(δ-phthalimidobutyl)-2''-N-acetyl-Aminoglycoside-XK-88-5, add 5 ml. of 90% aqueous hydrazine and heat under reflux for 48 hours under an atmosphere of nitrogen. Pour the reaction solution into a large volume of tetrahydrofuran and collect by filtration the resulting precipitate comprising 1-N-(δ-aminobutyl)-Aminoglycoside-XK-88-5.

Alternatively, the compound of this example is prepared as follows:

3. 4-Acetamidobutyraldehyde

Dissolve 5 gms. of 4-acetamidobutyraldehyde diethyl acetal in 75 ml. of distilled water and 5 ml. of 1 N sulfuric acid. Allow the solution to stand at room temperature until the hydrolysis is complete as determined by thin layer chromatography. Neutralize the solution with sodium bicarbonate, then saturate the solution with sodium chloride and extract with chloroform. Distill the combined chloroform extracts to a residue comprising 4-acetamidobutyraldehyde, which can be used without further purification in the following procedure.

4. 1-N-(δ-Acetamidobutyl)-2''-N-Acetyl-Aminoglycoside-XK-88-5

To 3 gms. of 2''-N-acetyl-Aminoglycoside-XK-88-5 in 120 ml. of distilled water add 0.1 N sulfuric acid until the solution is at about pH 2.5 - 3.5. Add 6 gms. of δ-acetamidobutyraldehyde prepared as described in the preceding procedure followed, after 10 minutes, with 600 mgms. of solid sodium cyanoborohydride. After 2 hours, concentrate the solution to a small volume and pour into methanol. Collect the resultant precipitate by filtration, dissolve in water and pass the aqueous solution through a column of Amberlite IRA-401S (OH$^-$) ion exchange resin. Evaporate the eluant and chromatograph the resultant residue on silica gel eluting with the lower phase of a chloroform:methanol:7% ammonium hydroxide solvent mixture. Evaporate the eluant to a residue comprising 1-N-(δ-acetamidobutyl)-2''-N-acetyl-Aminoglycoside-XK-88-5. Heat the residue with 10% aqueous potassium hydroxide at 100° C for 100 hours under an atmosphere of nitrogen, then neutralize with Amberlite IRC-50 ion exchange resin and elute with 2 N aqueous ammonium hydroxide. Concentrate the eluant and dissolve the resultant residue in water and lyophilize to obtain 1-N-(δ-aminobutyl)-Aminoglycoside-SK-88-5.

H. Other 1-N-(Aminoalkyl)-Aminoglycoside-XK-88-5 and 1-N-(Hydroxyaminoalkyl)-Aminoglycoside-XK-88-5 Derivatives In a manner similar to that described in Example 1G, treat the sulfuric acid addition salt of 2''-N-acetyl-Aminoglycoside-XK-88-5 in aqueous dimethylformamide with sodium cyanoborohydride and with each of the following amino substituted aldehydes:
1. 3-phthalimidopropanal,
2. 5-phthalimidopentanal,
3. 2-phthalimidopropanal,
4. 2-hydroxy-5-phthalimidopentanal,
5. 3-methyl-3-hydroxy-4-phthalimidobutanal,
6. 2-hydroxy-4-phthalimidobutanal,
7. 2-phthalimido-3-methylbutanal,
8. 2-hydroxy-3-phthalimidopropanal,
9. 2-hydroxy-2-methyl-3-phthalimidopropanal, and
10. 8-phthalimidooctanal.

In each case carry out the reaction in a manner similar to that described in Example 1A, and isolate and purify each of the resultant products in a manner similar to that described to obtain, respectively,
1. 1-N-(γ-phthalimidopropyl)-2''-N-acetyl-Aminoglycoside-XK-88-5, 2. 1-N-(ε-phthalimidopentyl)-2''-N-acetyl-Aminoglycoside-XK-88-5, 3. 1-N-(β-phthalimidopropyl)-2''-N-acetyl-Aminoglycoside-XK-88-5, 4. 1-N-(β-hydroxy-ε-phthalimidopentyl)-2''-N-acetyl-Aminoglycoside-XK-88-5, 5. 1-N-(γ-methyl-γ-hydroxy-δ-phthalimidobutyl)-2''-N-acetyl-Aminoglycoside-XK-88-5, 6. 1-N-(β-hydroxy-δ-phthalimidobutyl)-2''-N-acetyl-Aminoglycoside-XK-88-5, 7. 1-N-(β-phthalimido-γ-methylbutyl)-2''-N-acetyl-Aminoglycoside-XK-88-5, 8. 1-N-(ε-hydroxy-γ-phthalimidopropyl)-2''-N-acetyl-Aminoglycoside-XK-88-5, 9. 1-N-(β-hydroxy-β-methyl-γ-phthalimidopropyl)-2''-N-acetyl-Aminoglycoside-XK-88-5, 10. 1-N-(ω-phthalimidooctyl-2''-N-acetyl-Aminoglycoside-XK-88-5.

Treat each of the foregoing N-phthalimidoalkyl-2''-N-acetyl derivatives with ethanolic hydrazine hydrate as described in Example 1G(2) to obtain, respectively, 1. 1-N-(γ-aminopropyl)-Aminoglycoside-XK-88-5, 2. 1-N-(ε-aminopentyl)-Aminoglycoside-XK-88-5, 3. 1-N-(β-aminopropyl)-Aminoglycoside-XK-88-5, 4. 1-N-(β-hydroxy-ε-aminopentyl)-Aminoglycoside-XK-88-5, 5. 1-N-(γ-methyl-γ-hydroxy-δ-aminobutyl)-Aminoglycoside-XK-88-5, 6. 1-N-(β-hydroxy-δ-aminobutyl)-Aminoglycoside-XK-88-5, 7. 1-N-(β-amino-γ-methylbutyl)-Aminoglycoside-XK-88-5, 8. 1-N-(β-hydroxy-γ-aminopropyl)-Aminoglycoside-XK-88-5, 9. 1-N-(β-hydroxy-β-methyl-γ-aminopropyl)-Aminoglycoside-XK-88-5, and 10. 1-N-(ω-aminooctyl)-Aminoglycoside-XK-88-5.

I. Alkylaminoalkyl Derivatives and Other Hydroxyaminoalkyl Derivatives of Aminoglycoside-XK-88-5

1. 1-N-(β-methylaminoethyl)-Aminoglycoside-XK-88-5

In a manner similar to that described in Example 1A, treat 2''-N-acetyl-Aminoglycoside-XK-88-5 in water with 1 N sulfuric acid and 2-(N-methylacetamido)acetaldehyde followed by sodium cyanoborohydride. Isolate the resultant product in a manner similar to that described to obtain 1-N-(β-(N-methylacetamido)-2''-N-acetyl-Aminoglycoside-XK-88-5.

Treat the foregoing N-acetylated intermedite with 10% aqueous sodium hydroxide for 100 hours at 100° C. Cool the reaction solution and add to a column of Amberlite IRC-50 ion exchange resin. Wash the column with water and elute with 2 M ammonium hydroxide, concentrate the combined eluates in vacuo to a volume of about 100 ml., then lyophilize to a residue comprising 1-N-(β-methylaminoethyl)-Aminoglycoside-XK-88-5. Purify by chromatography in the manner of Example 1A(1).

2. In the procedure described in above Example 1-I(1), substitute for 2-(N-methylacetamido)acetaldehyde other aldehydes suc as 2-acetamido-3-hydroxyoctanal, or 2-acetamido-4-pentenal as aldehyde reagents to obtain the corresponding 1-N-(aminoalkyl) derivative, e.g. 1-N-(β-amino-γ-hydroxyoctyl)-Aminoglycoside-XK-88-5 and 1-N-(β-amino-δ-pentenyl)-Aminoglycoside-XK-88-5, respectively.

EXAMPLE 2

1-N-ALKYL DERIVATIVES OF AMINOGLYCOSIDE-XK-88-1, -3, AND -5

A. 1-N-Ethyl Derivatives of Aminoglycoside-XK-88-1, -3, and -5

Carry out the procedure of Example 1A(1) on each of Aminoglycoside-XK-88-1, Aminoglycoside-XK-88-3 and Aminoglycoside-XK-88-5 to obtain respectively, 1-N-ethyl-Aminoglycoside-XK-88-1, 1-N-ethyl-Aminoglycoside-XK-88-3 and 1-N-ethyl-Aminoglycoside-XK-88-5.

B. Other 1-N-Alkyl Derivatives of Aminoglycoside-XK-88-1, -3 and -5

React each of Aminoglycoside-XK-88-1, -3 and -5 in a manner similar to that described in Example 1A(1) but utilizing instead of acetaldehyde other aldehydes, e.g. the aldehydes utilized in each of procedures 1D through 1-I to obtain the corresponding 1-N-alkyl-Aminoglycoside-XK-88-1, 1-N-alkyl-Aminoglycoside-XK-88-3 and 1-N-alkyl-Aminoglycoside-XK-88-5, respectively.

EXAMPLE 3

ACID ADDTION SALTS

A. Sulfate Salts (Sulfuric Acid Addition Salts)

Dissolve 5.0 grams of 1-N-ethyl-Aminoglycoside-XK-88-5 in 25 ml. of water and adjust the pH of the solution to 4.5 with 1 N sulfuric acid. Pour into about 300 milliters of methanol with vigorous agitation, continue the agitation for about 10–20 minutes and filter. Wash the precipitate with methanol and dry at about 60° C in vacuo to obtain the sulfate salt of 1-N-ethyl-Aminoglycoside-XK-88-5.

In like manner, the sulfate salt of the compounds of Examples 1D through 1-I, and 2, are also prepared.

B. Hydrochloride Salts

Dissolve 5.0 grams of 1-N-ethyl-Aminoglycoside-XK-88-5 in 25 milliters of water. Acidify with 2 N hydrochloric acid to pH 5. Lyophilize to obtain 1-N-ethyl-Aminoglycoside-XK-88-5 hydrochloride.

In like manner, the hydrochloride salt of the compounds of Examples 1D through 1-I and 2, are also prepared.

The present invention includes within its scope pharmaceutical compositions comprising our novel 1-N-X-4,6-di-0-(aminoglycosyl)-2-deoxystreptamines with a compatible, pharmaceutically acceptable carrier or coating. Also included within our invention is the method of eliciting an antibacterial response in a warm-blooded animal having a susceptible bacterial infection which comprises administering to said animal a non-toxic, antibacterially effective amount of a member selected from the group consisting of a 1-N-X-Aminoglycoside-XK-88-1, 1-N-X-Aminoglycoside-XK-88-3, and 1-N-X-Aminoglycoside-XK-88-5, wherein X is an alkyl substituent selected from the group consisting of alkyl, alkenyl, aralkyl, cycloalkylalkyl, hydroxyalkyl, aminoalkyl, alkylaminoalkyl, aminohydroxyalkyl, and alkylaminohydroxyalkyl, said alkyl substituent having up to 8 carbon atoms and, when said alkyl substituent is substituted by both hydroxyl and amino functions, only one of said functions can be attached to any one carbon atom, and pharmaceutically acceptable acid addition salts thereof.

As discussed hereinabove, the 1-N-alkyl-4,6-di-O-(aminoglycosyl)-2-deoxystreptamines of this invention such as defined by formulae I, II and III (particularly 1-N-X-Aminoglycoside-XK-88-5) and the non-toxic, pharmaceutically acceptable acid addition salts thereof are broad spectrum antibacterial agents. Thus, the compounds of this invention can be used alone or in combination with other antibiotic agents to prevent the growth or reduce the number of bacteria in various environments. They may be used, for example, to disinfect laboratory glassware, dental and medical equipment contaminated with Staphylococcus aureus or other bacteria inhibited by the 1-N-alkyl derivatives of this invention. The activity of the 1-N-alkyl-4,6-di-O-(aminoglycosyl)-2-deoxystreptamines against gram-negative bacteria renders them useful for combating infections caused by gram-negative organisms, e.g. species of Proteus and Pseudomonas. Our 1-N-alkyl-4,6-di-O-(aminoglycosyl)-2-deoxystreptamines, e.g. 1-N-ethyl-Aminoglycoside-XK-88-5 have veterinary applications, particularly in the treatment of mastitis in cattle and Salmonella induced diarrhea in domestic animals such as the dog and the cat.

In general, the dosage administered of the 1-N-alkyl-4,6-di-O-(aminoglycosyl)-2-deoxystreptamines will be dependent upon the age and weight of the animal species being treated, the mode of administration, and the type and severity of bacterial infection being prevented or reduced. In general, the dosage of 1-N-alkyl-4,6-di-O-(aminoglycosyl)-2-deoxystreptamine employed to combat a given bacterial infection will be similar to the dosage requirements of the corresponding 1-N-unsubstituted-4,6-di-O-(aminoglycosyl)-2-deoxystreptamines. Additionally, the 1-N-alkyl-4,6-di-O-(aminoglycosyl)-l2-deoxystreptamines of formulae I, II and III, particularly those defined by formula III, e.g. 1-N-alkyl-Aminoglycoside-XK-88-5, wherein said alkyl has up to 4 carbon atoms, especially the 1-N-ethyl and 1-N-propyl derivatives, possess improved therapeutic activity compared to the 1-N-unsubstituted precursors.

The 1-N-alkyl-4,6-di-O-(aminoglycosyl)-2-deoxystreptamines of formulae I, II and III and the pharmaceutically acceptable acid addition salts thereof, may be administered orally. They may also be applied topically in the form of ointments, both hydrophilic and hydrophobic, in the form of lotions which may be aqueous, non-aqueous or of the emulsion type or in the form of creams. Pharmaceutical carriers useful in the preparation of such formulations will include, for example, such substances as water, oils, greases, polyesters, polyols and the like.

For oral administration, the 1-N-alkyl-4,6-di-O-(aminoglycosyl)-2-deoxystreptamine antibacterials of this invention may be compounded in the form of tablets, capsules, elixirs or the like or may even be admixed with aminal feed. It is in these dosage forms that the antibacterials are most effective for treating bacterial infections of the gastrointestinal tract, which infections cause diarrhea.

In general, the topical preparations will contain from about 0.1 to about 3.0 gms. of 1-N-alkyl-4,6-di-O-(aminoglycosyl)-2-deoxystreptamines of formulae I, II and III, per 100 gms. of ointment, creams or lotion. The topical preparations are usually applied gently to lesions from about 2 to about 5 times a day.

The antibacterials of this invention may be utilized in liquid form such as solutions, suspensions and the like for otic and optic use and may also be administered parenterally via intramuscular injection. The injectable solution or suspension will usually be administered at from about 1 mg. to about 15 mg. of antibacterial per kilogram of body weight per day divided into about 2 to about 4 doses. The precise dose depends on the stage and severity of the infection, the susceptibility of the infecting organism to the antibacterial and the individual characteristics of the animal species being treated.

The following formulations are to exemplify some of the dosage forms in which the antibacterial agents of this invention and their derivatives may be employed:

Formulation 1

| Tablet | 10 mg. Tab. | 25 mg. Tab. | 100 mg. Tab. |
|---|---|---|---|
| 1-N-ethyl-Aminoglycoside-XK-88-5 | 10.50* mg. | 26.25* mg. | 105.00* mg. |
| Lactose, impalpable powder | 197.50 mg. | 171.25 mg. | 126.00 mg. |
| Corn Starch | 25.00 mg. | 25.00 mg. | 35.00 mg. |
| Polyvinylpyrrolidone | 7.50 mg. | 7.50 mg. | 7.50 mg. |
| Magnesium Stearate | 2.50 mg. | 2.50 mg. | 3.50 mg. |

*5% excess

Procedure

Prepare a slurry consisting of the 1-N-ethyl-Aminoglycoside-XK-88-5, lactose and polyvinylpyrrolidone. Spray dry the slurry. Add the corn starch and magnesium stearate. Mix and compress into tablets.

Formulation 2

| Ointment | |
|---|---|
| 1-N-ethyl-Aminoglycoside-XK-88-5 | 1.0 gm. |
| Methyl paraben U.S.P. | 0.5 gm. |
| Propyl paraben U.S.P. | 0.1 gm. |
| Petrolatum to | 1000 gm. |

Procedure

1. Melt the petrolatum.
2. Mix the 1-N-ethyl-Aminoglycoside-XK-88-5, methyl paraben and propyl pareben with about 10% of the molten petrolatum.
3. Pass the mixture through a colloid mill.
4. Add the remainder of the petrolatum with agitation and cool the mixture until it becomes semi-solid. At this stage the product may be put into suitable containers.

Ointments of 1-N-alkyl-4,6-di-O-(aminoglycosyl)-2-deoxystreptamines of formulae I, II and III, and of the acid addition salts thereof are prepared by substituting an equivalent quantity of 1-N-alkyl-4,6-di-O-(aminoglycosyl)-2-deoxystreptamines or acid addition salt for 1-N-ethyl-Aminoglycoside-XK-88-5 in the foregoing example and by following substantially the procedure of the example.

Formulation 3

| Injectable Solution | Per 2.0 ml. vial | Per 50 Liters |
| --- | --- | --- |
| 1-N-ethyl-Aminoglycoside-XK-88-5 sulfate | 84.0 mgs.* | 2100.0 gms.* |
| Methyl paraben, U.S.P. | 3.6 mgs. | 90.0 gms. |
| Propyl paraben, U.S.P. | 0.4 mgs. | 10.0 gms. |
| Sodium bisulfite, U.S.P. | 6.4 mgs. | 160.0 gms. |
| Disodium Ethylenediamine tetraacetate dihydrate, R.G. | 0.2 mgs. | 5.0 gms. |
| Water, U.S.P. q.s. | 2.0 ml. | 50.0 liters |

*Includes a 5 % manufacturing overcharge.

Procedure: For a 50.0 liter batch

Charge approximately 35 liters of water for injection to a suitable stainless steel jacketed vessel and heat to about 70° C. Charge the methylparaben and propylparaben to the heated water for injection and dissolve with agitation. When the parabens are completely dissolved, cool the contents of the tank to 25°–30° C by circulating cold water through the tank jacket. Sparge the solution with nitrogen gas for at least 10 minutes and keep covered with nitrogen during subsequent processing. Charge and dissolve the disodium EDTA and sodium bisulfite. Charge and dissolve the 1-N-ethyl-Aminoglycoside-XK-88-5 sulfate. Bring the batch volume up to 50.0 liters with water for injection and agitate until homogenous.

Under sterile conditions, filter the solution through a suitable bacteria retentive filter collecting the filtrate in a filling tank.

Fill the filtrate aseptically into sterile pyrogen-free multiple dose vials, stopper and seal.

In like manner, injectable solutions of 1-N-propyl-Aminoglycoside-XK-88-5, 1-N-ethyl-Aminoglycoside-XK-88-1, 1-N-ethyl-Aminoglycoside-XK-88-3, and especially acid addition salts of such antibacterial agents, may be prepared by substituting an equivalent quantity of such compounds for 1-N-ethyl-Aminoglycoside-XK-88-5 sulfate and by following the procedure set forth above.

We claim:

1. A 1-N-X-4,6-di-O-(aminoglycosyl)-2-deoxystreptamine selected from the group consisting of 1-N-X-Aminoglycoside-XK-88-1, 1-N-X-Aminoglycoside-XK-88-3, and 1-N-X-Aminoglycoside-XK-88-5;
   wherein X is an alkyl substituent selected from the group consisting of alkyl, alkenyl, aralkyl, hydroxyalkyl, cycloalkylalkyl, aminoalkyl, alkylaminoalkyl, aminohydroxyalkyl, and alkylaminohydroxyalkyl, said alkyl substituent having up to 8 carbon atoms, the carbon in said alkyl substituent adjacent to the aminoglycoside nitrogen being unsubstituted, and when said alkyl substituent is substituted by both hydroxyl and amino functions, only one of said functions can be attached at any one carbon atom;
   and the pharmaceutically acceptable acid addition salts thereof.

2. A compound of claim 1 wherein X is an alkyl having up to 4 carbon atoms.

3. A compound of claim 1 which is 1-N-X-Aminoglycoside-XK-88-5, X being as defined in claim 1.

4. A compound of claim 1 which is 1-N-X-Aminoglycoside-XK-88-5 wherein X is an alkyl having 2 to 4 carbon atoms.

5. 1-N-ethyl-Aminoglycoside-XK-88-5 of claim 4.

6. 1-N-propyl-Aminoglycoside-XK-88-5 of claim 4.

7. 1-N-(γ-aminopropyl)-Aminoglycoside-XK-88-5 of claim 4.

8. 1-N-(δ-aminobutyl)-Aminoglycoside-XK-88-5 of claim 4.

* * * * *

UNITED STATES PATENT OFFICE
CERTIFICATE OF CORRECTION

Patent No. 4,002,608  Dated January 11, 1977

Inventor(s) Peter J. L. Daniels et al

It is certified that error appears in the above-identified patent and that said Letters Patent are hereby corrected as shown below:

Column 2, line 41, "β-amino-$\varepsilon$-methylbutyl" should read ---β-amino-$\gamma$-methylbutyl---; line 49, "β-hydroxy-$\delta\delta$-aminobutyl," should read ---β-hydroxy-$\delta$-aminobutyl,---; lines 50 and 51, "-$\varepsilon$-aminopropyl," should read ---$\gamma$-aminopropyl,---; line 51, "-$\varepsilon$-aminopropyl," should read ---$\gamma$-aminopropyl,---.
Column 7, line 67, "form the" should read --to form the---.
Column 13, line 13, "-($\varepsilon$-hydroxy-" should read ---(β-hydroxy--.
Column 15, line 47, "-12-deoxy-" should read ---2-deoxy---.
Column 15, line 68, "aminal" should read ---animal---.

Signed and Sealed this

Fifth Day of April 1977

[SEAL]

Attest:

RUTH C. MASON
Attesting Officer

C. MARSHALL DANN
Commissioner of Patents and Trademarks